(12) United States Patent
Cao

(10) Patent No.: US 12,190,502 B2
(45) Date of Patent: Jan. 7, 2025

(54) SYSTEMS AND METHODS FOR IMAGE OPTIMIZATION

(71) Applicant: SHANGHAI UNITED IMAGING HEALTHCARE CO., LTD., Shanghai (CN)

(72) Inventor: Wenjing Cao, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 662 days.

(21) Appl. No.: 17/124,450

(22) Filed: Dec. 16, 2020

(65) Prior Publication Data
US 2021/0142476 A1 May 13, 2021

Related U.S. Application Data

(63) Continuation of application No. PCT/CN2020/090862, filed on May 18, 2020.

(51) Int. Cl.
G06T 7/00 (2017.01)
G06T 5/50 (2006.01)
(Continued)

(52) U.S. Cl.
CPC .............. *G06T 7/0012* (2013.01); *G06T 5/50* (2013.01); *G06T 5/70* (2024.01); *G06T 5/73* (2024.01); *G06T 5/90* (2024.01); *G16H 30/40* (2018.01); *G16H 50/20* (2018.01); *G06T 2207/10116* (2013.01); *G06T 2207/20081* (2013.01);
(Continued)

(58) Field of Classification Search
CPC ....... G06T 7/0012; G06T 5/002; G06T 5/003; G06T 5/007; G06T 5/50; G06T 2207/10116; G06T 2207/20081; G06T 2207/20084; G06T 2207/20182; G06T 2207/30004; G06T 2207/30168; G06T 5/001; G06T 2210/41; G06T 11/008; G06T 2207/10081; G16H 30/40; G16H 50/20
See application file for complete search history.

(56) References Cited

U.S. PATENT DOCUMENTS 4,456,926 A 6/1984 Kruger et al.
2004/0068167 A1 4/2004 Hsieh et al.
(Continued)

FOREIGN PATENT DOCUMENTS

CA 2455088 A1 8/2004
CN 101156780 A 4/2008
(Continued)

OTHER PUBLICATIONS

The Extended European Search Report in European Application No. 20936697.0 mailed on Jan. 16, 2023, 9 pages.
(Continued)

*Primary Examiner* — Jianxun Yang
(74) *Attorney, Agent, or Firm* — METIS IP LLC

(57) ABSTRACT

Systems and methods for image optimization are provided. The system may obtain an image to be processed. The system may determine a quality feature of the image. The system may input the image and the quality feature into an image processing model. The system may also determine an optimized image of the image based on an output of the image processing model.

19 Claims, 9 Drawing Sheets

(51) Int. Cl.
  *G06T 5/70*     (2024.01)
  *G06T 5/73*     (2024.01)
  *G06T 5/90*     (2024.01)
  *G16H 30/40*    (2018.01)
  *G16H 50/20*    (2018.01)

(52) U.S. Cl.
  CPC ............... *G06T 2207/20084* (2013.01); *G06T 2207/20182* (2013.01); *G06T 2207/30004* (2013.01); *G06T 2207/30168* (2013.01)

(56) References Cited

U.S. PATENT DOCUMENTS

| | | |
|---|---|---|
| 2008/0108895 A1 | 5/2008 | Sabol et al. |
| 2014/0152800 A1 | 6/2014 | Fomitchov et al. |
| 2014/0307847 A1 | 10/2014 | Schmidt et al. |
| 2014/0369577 A1 | 12/2014 | Collins et al. |
| 2015/0359501 A1 | 12/2015 | Eronen et al. |
| 2017/0103512 A1* | 4/2017 | Mailhe ................. G06V 10/993 |
| 2017/0143312 A1 | 5/2017 | Hedlund et al. |
| 2017/0337713 A1 | 11/2017 | Hoelzer et al. |
| 2017/0372193 A1 | 12/2017 | Mailhe et al. |
| 2020/0027251 A1 | 1/2020 | Demesmaeker et al. |
| 2020/0043204 A1 | 2/2020 | Fu et al. |
| 2020/0104711 A1* | 4/2020 | Aytekin ................. G06N 3/045 |
| 2020/0126231 A1 | 4/2020 | Hu et al. |
| 2020/0372682 A1 | 11/2020 | Kim et al. |
| 2020/0380737 A1 | 12/2020 | Bao et al. |
| 2021/0248765 A1* | 8/2021 | Zhang ....................... G06T 7/55 |

FOREIGN PATENT DOCUMENTS

| | | |
|---|---|---|
| CN | 104318524 A | 1/2015 |
| CN | 106485680 A | 3/2017 |
| CN | 106952239 A | 7/2017 |
| CN | 107301662 A | 10/2017 |
| CN | 107341516 A | 11/2017 |
| CN | 108881708 A | 11/2018 |
| CN | 109242788 A | 1/2019 |
| CN | 110151210 A | 8/2019 |
| CN | 110490118 A | 11/2019 |
| CN | 110610463 A | 12/2019 |
| CN | 110660123 A | 1/2020 |
| CN | 110853742 A | 2/2020 |
| EP | 3485815 A1 | 5/2019 |
| WO | 2019033390 A1 | 2/2019 |
| WO | 2019114027 A1 | 6/2019 |

OTHER PUBLICATIONS

International Search Report in PCT/CN2021/094461 mailed on Aug. 16, 2021, 7 pages.
International Search Report in PCT/CN2020/090862 mailed on Feb. 20, 2021, 4 pages.
Written Opinion in PCT/CN2020/090862 mailed on Feb. 19, 2021, 4 pages.
The Extended European Search Report in European Application No. 21808874.8 mailed on Sep. 13, 2023, 8 pages.
Yan, Qiujuan, System Constscfion and Optimization of Imaging Quality for Photon Counting Detector, Master's Electronic Journal, 2020, 72 pages.

* cited by examiner

SYSTEMS AND METHODS FOR IMAGE OPTIMIZATION

CROSS-REFERENCE TO RELATED APPLICATIONS

This application is a Continuation of International Application No. PCT/CN2020/090862 filed on May 18, 2020, which designates the United States of America, the entire contents of which are hereby incorporated by reference.

TECHNICAL FIELD

The present disclosure relates to the field of image processing, and in particular, to systems and methods for image optimization.

BACKGROUND

With the development of medical imaging technologies, noise or artifact reduction becomes more and more important during medical image processing. Currently, machine learning technologies can be applied to reduce noises and/or artifacts in images. However, different images correspond to different noise levels or artifact levels, which may result in that traditional machine learning technology cannot achieve relatively good noise or artifact reduction effect. Therefore, it is desirable to provide improved systems and methods for image optimization, which can improve the performance of the machine learning model in noise and/or artifact reduction, thereby improving the effect of medical image processing.

SUMMARY

In an aspect of the present disclosure, a method for image optimization is provided. The method may include obtaining an image to be processed. The method may also include determining a quality feature of the image. Further, the method may include inputting the image and the quality feature into an image processing model and determining an optimized image of the image based on an output of the image processing model.

In some embodiments, the method further may include selecting the image processing model based on an initial feature of the image to be processed. The initial feature may include at least one of a feature associated with an object included in the image, a feature associated with a type of a scanning device upon which the image is obtained, or a reconstruction algorithm based on which the image is obtained.

In some embodiments, the quality feature may include at least one of a noise feature, an artifact feature, a gray distribution, a global gray scale, a resolution, or a contrast of the image.

In some embodiments, the noise feature may include at least one of a noise distribution, a noise intensity, or a noise rate. The artifact feature may include at least one of an artifact distribution, an artifact intensity, or an artifact rate.

In some embodiments, the image processing model may be obtained by a training process. The training process may include obtaining a plurality of training samples. Each of the plurality of training samples may include a sample image and a sample quality feature of the sample image. The training process may also include obtaining the image processing model by training a preliminary image processing model based on the plurality of training samples. A loss function of the image processing model may be positively related to a quality weight. The quality weight may be determined based on the sample quality feature.

In some embodiments, the sample quality feature may include at least one of a sample noise feature, a sample artifact feature, a sample gray distribution, a sample global gray scale, a sample resolution, or a sample contrast of the sample image.

In some embodiments, the sample noise feature may include at least one of a sample noise distribution, a sample noise intensity, or a sample noise rate. The sample artifact feature may include at least one of a sample artifact distribution, a sample artifact intensity, or a sample artifact rate.

In some embodiments, the quality weight may be positively related to the sample resolution, the quality weight may be negatively related to the sample noise intensity, the quality weight may be negatively related to the sample artifact intensity, or the quality weight may be negatively related to the sample contrast.

In some embodiments, the image processing model may be obtained by a training process. The training process may include obtaining a plurality of qualified images associated with a scanning device type. The training process may also include generating a plurality of sample images by preprocessing the plurality of qualified images. The preprocessing may include at least one of a segmentation, a noise addition, or an artifact addition. Further, the training process may include obtaining the image processing model by training a preliminary image processing model based on the plurality of sample images and a plurality of sample quality features corresponding to the plurality of sample images.

In some embodiments, the image processing model may be obtained by a training process. The training process may include obtaining a plurality of qualified images associated with an object type. The training process may also include generating a plurality of sample images by preprocessing the plurality of qualified images. The preprocessing may include at least one of a segmentation, a noise addition, or an artifact addition. Further, the training process may include obtaining the image processing model by training a preliminary image processing model based on the plurality of sample images and a plurality of sample quality features corresponding to the plurality of sample images.

In another aspect of the present disclosure, a system for image optimization is provided. The system may include at least one storage device including a set of instructions, and at least one processor configured to communicate with the at least one storage device. When executing the set of instructions, the at least one processor may direct the system to perform the following operations. The at least processor may obtain an image to be processed. The at least one processor may determine a quality feature of the image. Further, the at least one processor may input the image and the quality feature into an image processing model and determining an optimized image of the image based on an output of the image processing model.

In some embodiments, the at least one processor may further select the image processing model based on an initial feature of the image to be processed. The initial feature may include at least one of a feature associated with an object included in the image, a feature associated with a type of a scanning device upon which the image may be obtained, or a reconstruction algorithm based on which the image is obtained.

In some embodiments, the quality feature may include at least one of a noise feature, an artifact feature, a gray distribution, a global gray scale, a resolution, or a contrast of the image.

In some embodiments, the noise feature may include at least one of a noise distribution, a noise intensity, or a noise rate. The artifact feature may include at least one of an artifact distribution, an artifact intensity, or an artifact rate.

In some embodiments, the image processing model may be obtained by a training process. The training process may include obtaining a plurality of training samples. Each of the plurality of training samples may include a sample image and a sample quality feature of the sample image. The training process may also include obtaining the image processing model by training a preliminary image processing model based on the plurality of training samples. A loss function of the image processing model may be positively related to a quality weight. The quality weight may be determined based on the sample quality feature.

In some embodiments, the sample quality feature may include at least one of a sample noise feature, a sample artifact feature, a sample gray distribution, a sample global gray scale, a sample resolution, or a sample contrast of the sample image.

In some embodiments, the sample noise feature may include at least one of a sample noise distribution, a sample noise intensity, or a sample noise rate. The sample artifact feature may include at least one of a sample artifact distribution, a sample artifact intensity, or a sample artifact rate.

In some embodiments, the quality weight may be positively related to the sample resolution, the quality weight may be negatively related to the sample noise intensity, the quality weight may be negatively related to the sample artifact intensity, or the quality weight may be negatively related to the sample contrast.

In some embodiments, the image processing model may correspond to a scanning device type. The image processing model may be obtained by a training process. The training process may include obtaining a plurality of qualified images associated with the scanning device type. The training process may also include generating a plurality of sample images by preprocessing the plurality of qualified images. The preprocessing may include at least one of a segmentation, a noise addition, or an artifact addition. Further, the training process may include obtaining the image processing model corresponding to the scanning device type by training a preliminary image processing model based on the plurality of sample images and a plurality of sample quality features corresponding to the plurality of sample images.

In some embodiments, the image processing model may correspond to an object type. The image processing model may be obtained by a training process. The training process may include obtaining a plurality of qualified images associated with the object type. The training process may also include generating a plurality of sample images by preprocessing the plurality of qualified images. The preprocessing may include at least one of a segmentation, a noise addition, or an artifact addition. Further, the training process may include obtaining the image processing model corresponding to the object type by training a preliminary image processing model based on the plurality of sample images and a plurality of sample quality features corresponding to the plurality of sample images.

In another aspect of the present disclosure, a non-transitory computer readable medium including executable instructions is provided. The executable instructions, when executed by at least one processor, may direct the at least one processor to perform a method. The method may include obtaining an image to be processed. The method may also include determining a quality feature of the image. Further, the method may include inputting the image and the quality feature into an image processing model and determining an optimized image of the image based on an output of the image processing model.

In another aspect of the present disclosure, a system for image optimization is provided. The system may include an obtaining module configured to obtain an image to be processed. The system may also include a feature determination module configured to determine a quality feature of the image. Further, the system may include an optimization module configured to input the image and the quality feature into an image processing model and determine an optimized image of the image based on an output of the image processing model.

In another aspect of the present disclosure, a method for image optimization is provided. The method may include obtaining raw image data to be processed. The method may also include determining a quality feature of the raw image data. The method may further include inputting the raw image data and the quality feature into an image processing model and determine optimized image data of the raw image data based on an output of the image processing model.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in detail of exemplary embodiments. These exemplary embodiments are described in detail with reference to the drawings. These embodiments are not limiting, and in these embodiments, the same number indicates the same structure, wherein.

DETAILED DESCRIPTION

Figure 1:
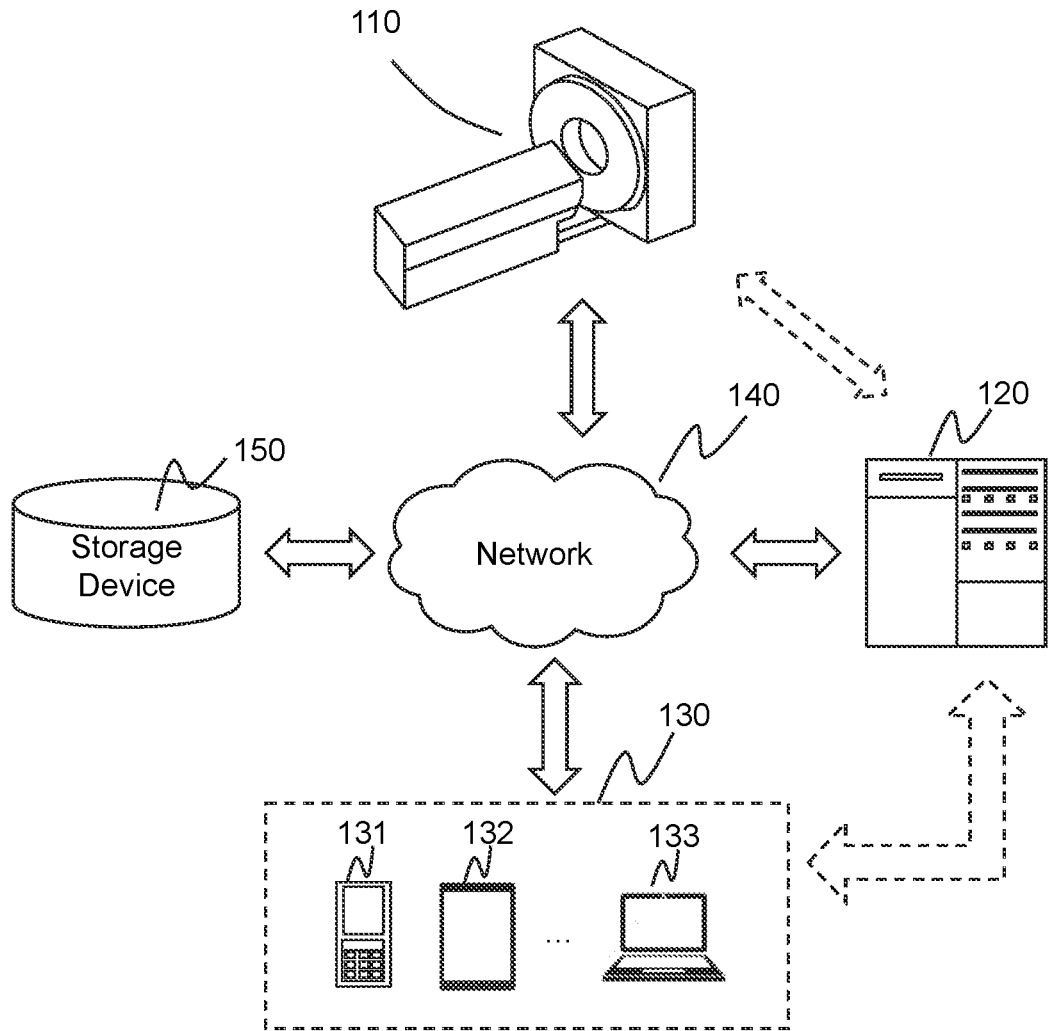
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the terms "system," "engine," "unit," "module," and/or "block" used herein are one method to distinguish different components, elements, parts, sections, or assemblies of different levels in ascending order. However, the terms may be displaced by another expression if they achieve the same purpose.

Generally, the words "module," "unit," or "block," as used herein, refer to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data) and/or images of various forms, including a two-dimensional (2D) image, a three-dimensional (3D) image, a four-dimensional (4D) image, etc.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging/treatment, such as for disease diagnostic, disease therapy, or research purposes. In some embodiments, the systems may include an imaging system. The imaging system may include a single modality system and/or a multi-modality system. The term "modality" used herein broadly refers to an imaging or treatment method or technology that gathers, generates, processes, and/or analyzes imaging information of a subject or treatments the subject. The single modality system may include, for example, an ultrasound imaging system, an X-ray imaging system, a computed tomography (CT) system, a magnetic resonance imaging (MRI) system, an ultrasonography system, a positron emission tomography (PET) system, an optical coherence tomography (OCT) imaging system, an ultrasound (US) imaging system, an intravascular ultrasound (IVUS) imaging system, a near-infrared spectroscopy (NIRS) imaging system, or the like, or any combination thereof. The multi-modality system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a positron emission tomography-magnetic resonance imaging (PET-MR) system, a digital subtraction angiography-magnetic resonance imaging (DSA-MRI) system, etc. In some embodiments, the medical system may include a treatment system. The treatment system may include a treatment plan system (TPS), image-guided radiotherapy (IGRT), etc. The image-guided radiotherapy (IGRT) may include a treatment device and an imaging device. The treatment device may include a linear accelerator, a cyclotron, a synchrotron, etc., configured to perform a radiotherapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc. It should be noted that the medical system described below is merely provided for illustration purposes, and not intended to limit the scope of the present disclosure.

In the present disclosure, the subject may include a biological object and/or a non-biological object. The biological subject may be a human being, an animal, a plant, or a specific portion, organ, and/or tissue thereof. For example, the subject may include a head, a neck, a thorax, a heart, a stomach, a blood vessel, a soft tissue, a tumor, a nodule, or the like, or any combination thereof. In some embodiments, the subject may be a man-made composition of organic and/or inorganic matters that are with or without life. The term "object" or "subject" are used interchangeably in the present disclosure.

In the present disclosure, a representation of an object (e.g., a patient, a subject, or a portion thereof) in an image may be referred to as an object for brevity. For instance, a representation of an organ or tissue (e.g., a heart, a liver, a lung) in an image may be referred to as an organ or tissue for brevity. Further, an image including a representation of an object may be referred to as an image of an object or an image including an object for brevity. Still further, an operation performed on a representation of an object in an image may be referred to as an operation performed on an object for brevity. For instance, a segmentation of a portion of an image including a representation of an organ or tissue from the image may be referred to as a segmentation of an organ or tissue for brevity.

An aspect of the present disclosure relates to systems and methods for image optimization. The system may obtain an image to be processed and determine a quality feature of the image. The quality feature may include at least one of a noise feature (e.g., a noise rate) or an artifact feature (e.g., an artifact rate). The system may input both the image and the quality feature into an image processing model. Further, the system may determine an optimized image of the image based on an output of the image processing model. According to some embodiments of the present disclosure, both the image and the quality feature of the image are input into the image processing model, that is, both global image information and quality feature of the image are taken into consideration, which improves the optimization effect of the image processing model. Further, the image processing model is trained based on a plurality of training samples with various quality levels and during the training process, the plurality of training samples correspond to different quality weights, which can ensure that the image processing model can efficiently and accurately process images with different quality levels, thereby improving the image optimization effect.

FIG. 1 is a schematic diagram illustrating an exemplary medical system according to some embodiments of the present disclosure. As illustrated, the medical system 100 may include a scanning device 110, a processing device 120, a terminal device 130, a network 140, and a storage device 150. The components of the medical system 100 may be connected in one or more of various ways. Mere by way of example, as illustrated in FIG. 1, the scanning device 110 may be connected to the processing device 120 through the network 140. As another example, the scanning device 110 may be connected to the processing device 120 directly (as indicated by the bi-directional arrow in dotted lines linking the scanning device 110 and the processing device 120). As a further example, the storage device 150 may be connected to the processing device 120 directly or through the network 140. As still a further example, the terminal device 130 may be connected to the processing device 120 directly (as indicated by the bi-directional arrow in dotted lines linking the terminal device 130 and the processing device 120) or through the network 140.

The scanning device 110 may be configured to acquire imaging data relating to at least one part of a subject. The scanning device 110 may scan the subject or a portion thereof that is located within its detection region and generate imaging data relating to the subject or the portion thereof. The imaging data relating to at least one part of a subject may include an image (e.g., an image slice), projection data, or a combination thereof. In some embodiments, the imaging data may be two-dimensional (2D) imaging data, three-dimensional (3D) imaging data, four-dimensional (4D) imaging data, or the like, or any combination thereof. In some embodiments, the scanning device 110 may include a single modality imaging device. For example, the scanning device 110 may include a digital subtraction angiography (DSA), a positron emission tomography (PET) device, a single-photon emission computed tomography (SPECT) device, a magnetic resonance imaging (MRI) device (also referred to as an MR device, an MR scanner), a computed tomography (CT) device, an ultrasonography scanner, a digital radiography (DR) scanner, or the like, or any combination thereof. In some embodiments, the scanning device 110 may include a multi-modality imaging device. Exemplary multi-modality imaging devices may include a PET-CT device, a PET-MR device, or the like, or a combination thereof. For illustration purposes, the present disclosure is described in connection with a CT device.

The processing device 120 may process data and/or information obtained from the scanning device 110, the terminal device 130, and/or the storage device 150. For example, the processing device 120 may obtain an image to be processed generated by the scanning device 110. The processing device 120 may determine a quality feature of the image and input the image and the quality feature into an image processing model. Further, the processing device 120 may determine an optimized image of the image based on an output of the image processing model. As another example, the processing device 120 may obtain a plurality of training samples and obtain the image processing model by training a preliminary image processing model based on the plurality of training samples. In some embodiments, the processing device 120 may include a central processing unit (CPU), a digital signal processor (DSP), a system on a chip (SoC), a microcontroller unit (MCU), or the like, or any combination thereof. In some embodiments, the processing device 120 may include a computer, a user console, a single server or a server group, etc. The server group may be centralized or distributed. In some embodiments, the processing device 120 may be local or remote. For example, the processing device 120 may access information and/or data stored in the scanning device 110, the terminal device 130, and/or the storage device 150 via the network 140. As another example, the processing device 120 may be directly connected to the scanning device 110, the terminal device 130 and/or the storage device 150 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 or a portion of the processing device 120 may be integrated into the scanning device 110. In some embodiments, the processing device 120 may be implemented by a computing device 200 including one or more components as described in FIG. 2.

The terminal device 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the smart mobile device may include a mobile phone, a personal digital assistant (PDA), a gaming device, a navigation device, a point of sale (POS) device, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal device 130 may be part of the processing device 120.

The network 140 may include any suitable network that can facilitate the exchange of information and/or data for the medical system 100. In some embodiments, one or more components (e.g., the scanning device 110, the processing device 120, the storage device 150, the terminal device 130) of the medical system 100 may communicate information and/or data with one or more other components of the medical system 100 via the network 140. For example, the processing device 120 may obtain data from the scanning device 110 via the network 140. As another example, the terminal device 130 may receive an optimized image from the processing device 120 via the network 140. In some embodiments, one or more components (e.g., the scanning device 110, the processing device 120, the storage device 150, the terminal device 130) of the medical system 100 may communicate information and/or data with one or more external resources such as an external database of a third party, etc. For example, the processing device 120 may obtain an image processing model from an external database of a vendor or manufacture that provides and/or updates the image processing model (e.g., a manufacture of the scanning device 110). The network 140 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 140 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 140 may include one or more network access points. For example, the network 140 may include wired and/or wireless network access points, such as base stations and/or internet exchange points, through which one or more components of the medical system 100 may be connected to the network 140 to exchange data and/or information.

The storage device 150 may store data, instructions, and/or any other information. In some embodiments, the storage device 150 may store data obtained from the scanning device 110, the terminal device 130, and/or the processing device 120. In some embodiments, the storage device 150 may store data and/or instructions that the processing device 120 may execute or use to perform exemplary methods/systems described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 140 to communicate with one or more other components (e.g., the scanning device 110, the processing device 120, the terminal device 130) of the medical system 100. One or more components of the medical system 100 may access the data or instructions stored in the storage device 150 via the network 140. In some embodiments, the storage device 150 may be directly connected to or communicate with one or more other components (e.g., the scanning device 110, the processing device 120, the terminal device 130) of the medical system 100. In some embodiments, the storage device 150 may be part of the processing device 120.

It should be noted that the above description of the medical system 100 is merely provided for the purposes of illustration, and not intended to limit the scope of the present disclosure. For persons having ordinary skills in the art, multiple variations and modifications may be made under the teachings of the present disclosure. For example, the medical system 100 may include one or more additional components and/or one or more components of the medical system 100 described above may be omitted. Additionally or alternatively, two or more components of the medical system 100 may be integrated into a single component. A component of the medical system 100 may be implemented on two or more sub-components.

Figure 2:
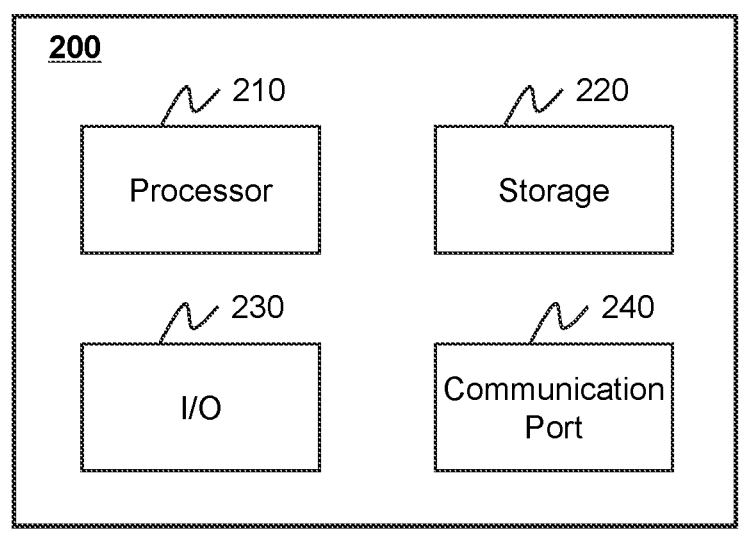
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device according to some embodiments of the present disclosure. The computing device 200 may be used to implement any component of the medical system 100 as described herein. For example, the processing device 120 and/or the terminal device 130 may be implemented on the computing device 200, respectively, via its hardware, software program, firmware, or a combination thereof. Although only one such computing device is shown for convenience, the computer functions relating to the medical system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program codes) and perform functions of the processing device 120 in accordance with techniques described herein. The computer instructions may include, for example, routines, programs, objects, components, signals, data structures, procedures, modules, and functions, which perform particular functions described herein. In some embodiments, the processor 210 may perform instructions obtained from the terminal device 130 and/or the storage device 150. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the scanning device 110, the terminal device 130, the storage device 150, or any other component of the medical system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, a camera capturing gestures, or the like, or a combination thereof. Exemplary output devices may include a display device, a loudspeaker, a printer, a projector, a 3D hologram, a light, a warning light, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 140) to facilitate data communications. The communication port 240 may establish connections between the processing device 120 and the scanning device 110, the terminal device 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
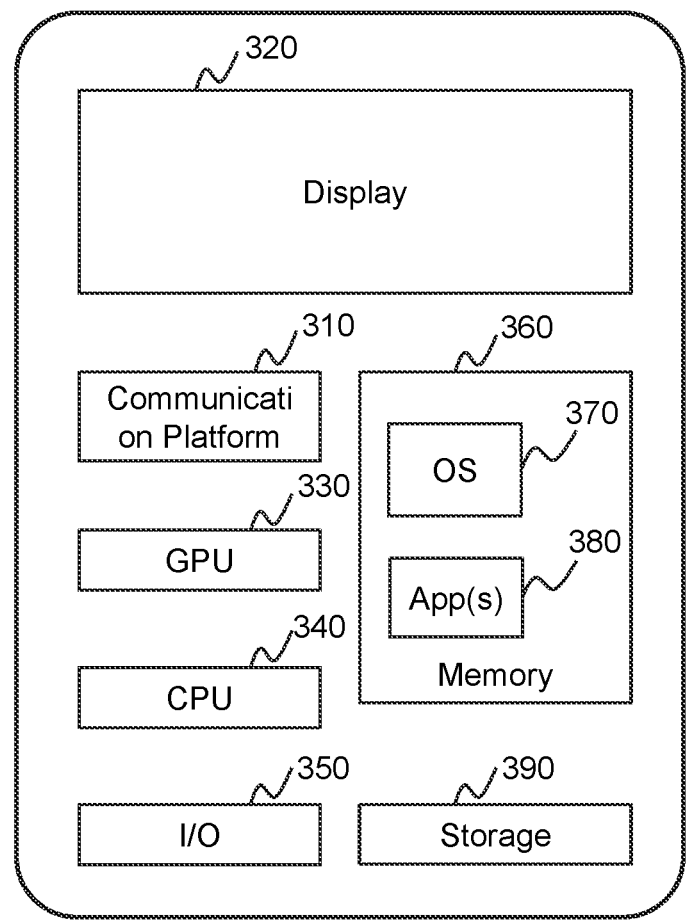
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, one or more components (e.g., a terminal device 130 and/or the processing device 120) of the medical system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the medical system via the network 140.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4A:
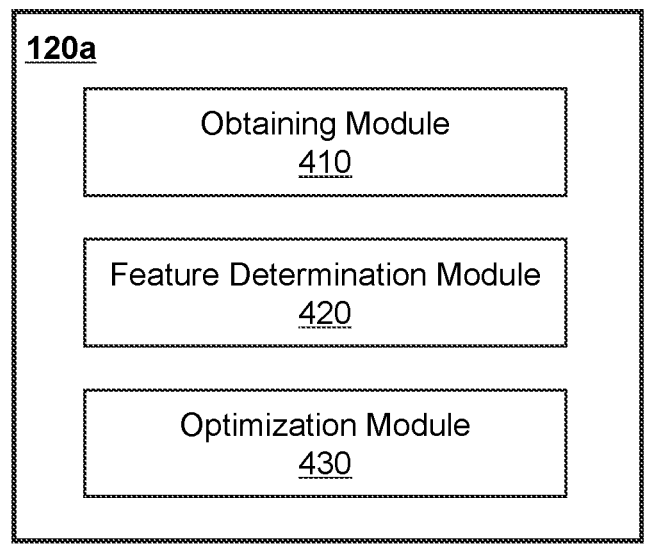
FIG. 4A and FIG. 4B are block diagrams illustrating exemplary processing devices according to some embodiments of the present disclosure.
Figure 4B:
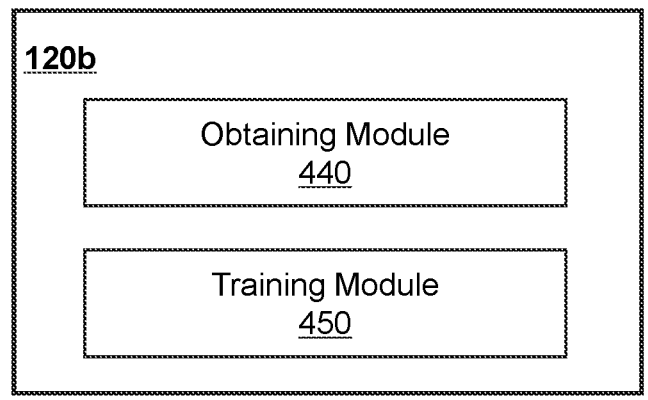

FIG. 4A and FIG. 4B are block diagrams illustrating exemplary processing devices according to some embodiments of the present disclosure. In some embodiments, as described in connection with FIG. 1, the processing device 120a and the processing device 120b may be embodiments of the processing device 120. In some embodiments, the processing device 120a and the processing device 120b may be implemented on a same device or separate devices. For example, both the processing device 120a and the processing device 120b may be implemented on the computing device 200. As another example, the processing devices 120a may be implemented on the terminal device 300 and the processing device 120b may be implemented on the computing device 200.

As illustrated in FIG. 4A, the processing device 120a may include an obtaining module 410, a feature determination module 420, and an optimization module 430.

The obtaining module 410 may be configured to obtain data and/or information from one or more components of the medical system 100. For example, the obtaining module 410 may obtain an image to be processed (also can be referred to as an "image to be optimized") from a storage device described elsewhere in the present disclosure. As used herein, the image to be processed may refer to an image (e.g., a 2D image, a 3D image, a 4D image) or raw image data (e.g., raw CT data acquired by the scanning device 110). For convenience, "image" is described as an example hereafter. As another example, the obtaining module 410 may obtain an image processing model from a storage device as described elsewhere in the present disclosure. The image processing model may be a machine learning model (e.g., a deep learning model). In some embodiments, the obtaining module 410 may select the image processing model according to an optimization target of the image. More descriptions regarding the image to be processed and the image processing model may be found elsewhere in the present disclosure (e.g., operations 510 and 530 and the descriptions thereof).

The feature determination module 420 may be configured to determine a quality feature of the image. In some embodiments, the quality feature of the image may include a noise feature, an artifact feature, a gray distribution (e.g., a distribution of pixel gray values of the image), a global gray scale (e.g., an average gray value of the pixel gray values, a weighted average gray value of the pixel gray values), a resolution (e.g., a sharpness degree of the image), a contrast (e.g., a grayscale contrast) of the image, or the like, or a combination thereof. In some embodiments, the feature determination module 420 may determine the quality feature of the image according to an optimization target (e.g., noise reduction, artifact reduction, resolution enhancement, contrast improvement) corresponding to the image. More descriptions regarding the quality feature of the image may be found elsewhere in the present disclosure (e.g., operation 520 and the description thereof).

The optimization module 430 may be configured to generate an optimized image of the image by application of an image processing model. For example, the optimization module 430 may input the image and the quality feature into the image processing model and determine the optimized image of the image based on an output of the image processing model. In some embodiments, the optimization module 430 may preprocess the image and input the preprocessed image and the quality feature into the image processing model. The optimization module 430 may determine the optimized image by post-processing the output of the image processing model. More descriptions regarding the generation of the optimized image of the image may be found elsewhere in the present disclosure (e.g., operations 530 and 540 in FIG. 5 and the descriptions thereof).

As illustrated in FIG. 4B, the processing device 120b may include an obtaining module 440 and a training module 450.

The obtaining module 440 may be configured to obtain data/information relating to training an image processing model from one or more components of the medical system 100. For example, the obtaining module 440 may obtain a plurality of training samples from a storage device as described elsewhere in the present disclosure. Each of the plurality of training samples may include a sample image, a sample quality feature of the sample image. As another example, the obtaining module 440 may obtain a plurality of qualified image associated with a scanning device type and/or an object type from a storage device as described elsewhere in the present disclosure. The obtaining module 440 may generate the plurality of sample images by preprocessing the plurality of qualified images. The preprocessing may include segmentation, noise addition, artifact addition, or the like, or any combination thereof. More descriptions regarding the plurality of training samples may be found elsewhere in the present disclosure (e.g., operation 610 in FIG. 6, operations 710 and 720 in FIG. 7, and operations 810 and 820 in FIG. 8 and the descriptions thereof).

The training module 450 may be configured to obtain an image processing model according to a training process. The image processing model may correspond to an object type and/or a scanning device type. In some embodiments, the training module 450 may train a preliminary image processing model based on the plurality of training samples. For example, the training module 450 may train the preliminary image processing model iteratively until a termination condition is satisfied. In response to that the termination condition is satisfied, the image processing model may be finalized. In some embodiments, the termination condition may relate to a value of a loss function. The loss function may be positively related to a quality weight which may be associated with a quality level of a sample image and may be determined based on the sample quality feature of the sample image. Different training samples may correspond to different quality weights. More descriptions regarding the obtaining of the image processing model may be found elsewhere in the present disclosure (e.g., operation 620 in FIG. 6, operation 730 in FIG. 7, and operation 830 in FIG. 8 and the descriptions thereof).

The modules in the processing device 120a and/or the processing device 120b may be connected to or communicated with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined into a single module, and any one of the modules may be divided into two or more units. In some embodiments, the processing device 120a and/or the processing device 120b may share two or more of the modules. For example, the processing device 120a and the processing device 120b may share a common obtaining module, that is, the obtaining module 410 and the obtaining module 440 may be implemented via a single module. In some embodiments, the processing device 120a and/or the processing device 120b may include one or more additional modules, such as a storage module (not shown) used for storing data. In some embodiments, the processing device 120a and the processing device 120b may be integrated into a single processing device.

Figure 5:
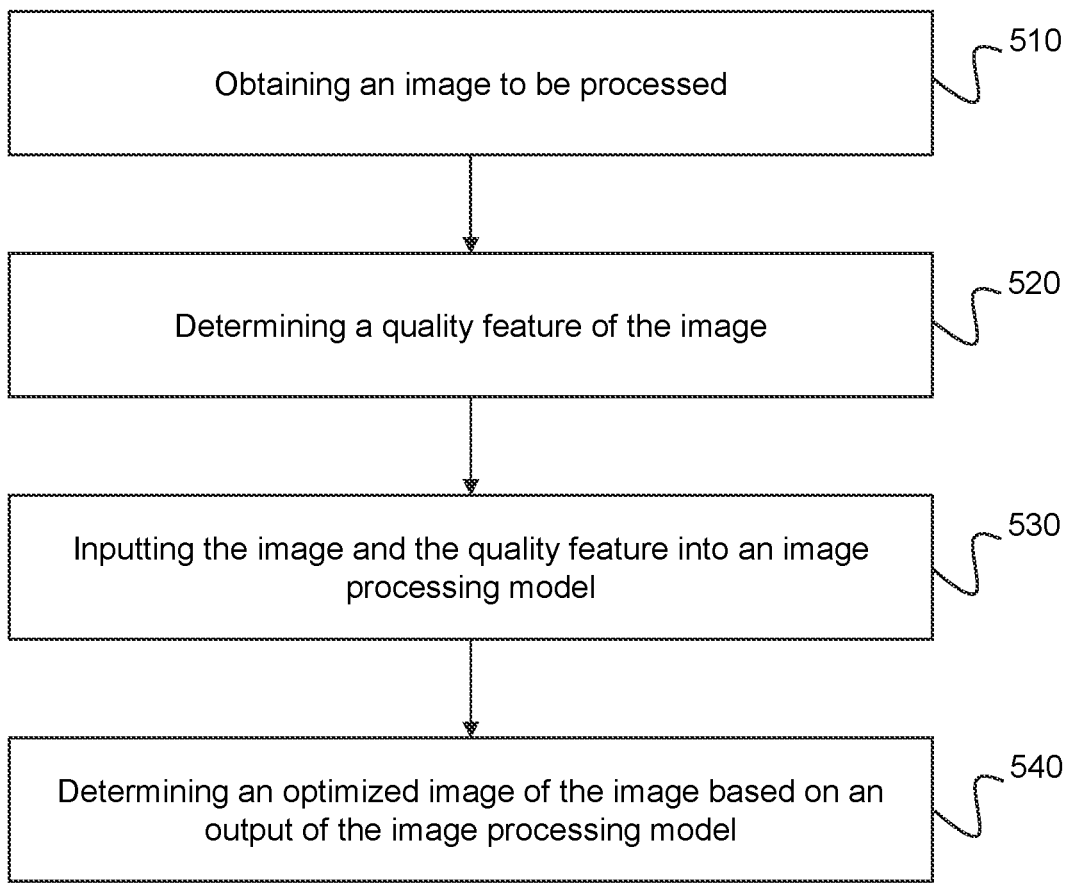
FIG. 5 is a flowchart illustrating an exemplary process for image optimization according to some embodiments of the present disclosure.

FIG. 5 is a flowchart illustrating an exemplary process for image optimization according to some embodiments of the present disclosure. In some embodiments, process 500 may be implemented as a set of instructions (e.g., an application) stored in a storage device (e.g., the storage device 150, the storage 220, and/or the storage 390). The processing device 120a (e.g., the processor 210, the CPU 340, and/or one or more modules illustrated in FIG. 4A) may execute the set of instructions, and when executing the instructions, the processing device 120a may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

In 510, the processing device 120a (e.g., the obtaining module 410) may obtain an image to be processed (also can be referred to as an "image to be optimized"). As used herein, the image to be processed may refer to an image (e.g., a 2D image, a 3D image, a 4D image) or raw image data (e.g., raw CT data acquired by the scanning device 110). For convenience, "image" is described as an example hereafter.

In some embodiments, the image to processed may be an image with a relatively low image quality, for example, an image including artifact(s), an image including noise(s), an image with a low signal to noise ratio (SNR), an image with a low contrast, an image with a low resolution, etc. As described in connection with FIG. 1, the image to be processed may include an X-ray image, a CT image, a PET image, an MR image, a SPECT image, or the like, or any combination thereof. For illustration purposes, the image to be processed is described in connection with a CT image. For example, the image to be processed may be a reconstructed CT image which includes noises and/or artifacts. The reconstructed CT image may be reconstructed based on raw CT data using a reconstruction algorithm. Exemplary reconstruction algorithms may include a Filter Back Projection (FBP) algorithm, an Algebraic Reconstruction Technique (ART), a Local Reconstruction Algorithm (LocalRA), an iterative reconstruction algorithm, or the like, or any combination thereof.

In some embodiments, the image may be pre-generated and stored in a storage device (e.g., the storage device 150, the storage 220, and/or the storage 390) disclosed elsewhere in the present disclosure. The processing device 120a may retrieve the image to be processed from the storage device. In some embodiments, the image may be generated by the processing device 120a. For example, the scanning device 110 may be directed to perform a scan on a subject to acquire scanning data of the subject and the processing device 120a may generate the image based on the scanning data.

In 520, the processing device 120a (e.g., the feature determination module 420) may determine a quality feature of the image.

In some embodiments, the quality feature of the image may include a noise feature, an artifact feature, a gray distribution (e.g., a distribution of pixel gray values of the image), a global gray scale (e.g., an average gray value of the pixel gray values, a weighted average gray value of the pixel gray values), a resolution (e.g., a sharpness degree of the image), a contrast (e.g., a grayscale contrast) of the image, or the like, or a combination thereof.

As used herein, a noise of an image refers to a random error in the image, which may result in an appearance of mottling, grain, texture, snowflake, etc. in the image. Exemplary noise features may include a noise distribution, a noise intensity, a global noise intensity, a noise rate, or the like, or any combination thereof. In some embodiments, a noise intensity may refer to a value of a noise pixel which reflect an amplitude of the noise in the noise pixel, accordingly, the noise distribution may reflect probability densities of noises with different noise intensities in the image; the global noise intensity may reflect an average noise intensity or a weighted average noise intensity in the image; and the noise rate may reflect a dispersion degree of the noise distribution. In some embodiments, the processing device 120a may determine the noise feature based on a statistical noise model and/or a probability density function (PDF) corresponding to the statistical noise model. For example, the processing device 120a may determine a representation (e.g., a curve, a value, a vector, a matrix) of the noise distribution according to the statistical noise model and/or the PDF. As another example, the processing device 120a may determine the global noise intensity based on an average value or a weighted value associated with the representation of the noise distribution. As a further example, the processing device 120a may determine the noise rate based on a variance and/or a standard deviation of the representation of the noise distribution. As a still further another example, for raw CT data, the processing device 120a may determine a statistic noise model corresponding to the raw CT data by estimating statistical noise characteristics of X-rays used to acquire the raw CT data. Further, the processing device 120a may determine noise feature(s) of the raw CT data based on the statistic noise model and a reconstruction algorithm which may be used to reconstruct the raw CT data. Exemplary statistical noise models may include a Gaussian noise model, an impulse noise model, a Rayleigh noise model, an exponential distribution noise model, a uniform distribution noise model, or the like, or any combination thereof. In some embodiments, the processing device 120a may determine the noise feature of the image using an image block algorithm, a filter algorithm, a spatial sampling algorithm, a Bayesian estimation algorithm, or the like, or any combination thereof.

As used herein, an artifact of an image refers to a portion of an image that does not correspond to any part that actually exists in the subject of the image, which may result in image distortion, image overlap, image loss, image blur, etc. Exemplary artifact features may include an artifact distribution, an artifact intensity, a global artifact intensity, an artifact rate, or the like, or any combination thereof. In some embodiments, an artifact intensity may refer to a value of an artifact pixel which reflects an intensity of the artifact in the artifact pixel. In some embodiments, the processing device 120a may identify an artifact in the image and determine the artifact intensity based on a feature (e.g., a texture, a shape) of the artifact. In some embodiments, the processing device 120a may determine the feature of the artifact using a feature extraction algorithm. Exemplary extraction algorithms may include a histogram of oriented gradients, a local binary pattern (LBP) algorithm, a scale invariant feature transform (SIFT) algorithm, a Haar-like algorithm, a gray-level co-occurrence matrix (GLCM) algorithm, a Hough transform algorithm, a Fourier transform algorithm, a Fourier shape deors algorithm, a shape factor algorithm, a finite element method (FEM) algorithm, a turning algorithm, a wavelet deor algorithm, etc. Further, similar to the noise feature, the artifact distribution may reflect probability densities of artifacts with different intensities in the image; the global artifact intensity may reflect an average artifact intensity or a weighted average artifact intensity in the image; and the artifact rate may reflect a dispersion degree of the artifact distribution. Similarly, the processing device 120a may also determine the artifact feature based on a statistical model and/or a probability density function (PDF) corresponding to the statistical model.

In some embodiments, the processing device 120a may determine the quality feature of the image according to an optimization target corresponding to the image. Exemplary optimization targets may include noise reduction, artifact reduction, resolution enhancement, contrast improvement, or the like, or any combination thereof. Merely by way of example, if the optimization target corresponding to the image is noise reduction, the processing device 120a may determine at least one noise feature of the image. As another example, if the optimization target corresponding to the image is artifact reduction, the processing device 120a may determine at least one artifact feature of the image. As a further example, if the optimization target corresponding to the image is resolution enhancement, the processing device 120a may determine at least one quality feature (e.g., a noise feature, an artifact feature, a resolution) associated with resolution enhancement.

In 530 the processing device 120a (e.g., the optimization module 430) may input the image and the quality feature into an image processing model.

In some embodiments, the image processing model may be a machine learning model that is configured to optimize the image based on the image and the quality feature of the image to achieve the optimization target corresponding to the image. In some embodiments, the image processing model may be a deep learning model. Exemplary deep learning models may include a deep neural network (DNN) model, a multi-layer perceptron (MLP) model, a conventional neural network (CNN) model, a generative adversarial network (GAN) model, a deep convolutional encoder-decoder (DCED) network model, or any other suitable model.

In some embodiments, the processing device 120a may select the image processing model based on an initial feature of the image to be processed. The initial feature may include a feature associated with an object included in the image, a feature associated with a type of a scanning device upon which the image is obtained, etc. For example, the processing device 120a may obtain one or more features (e.g., a shape, a color, a texture) associated with the object and determine an object type (e.g., a head, a chest, a lung) of the object based on the one or more features. Further, the processing device 120a may select an image processing model corresponding to the object type. As used herein, an image processing model corresponding to a specific object type may refer to that the image processing model (e.g., an image processing model corresponding to "chest") is trained based on a plurality of training samples (e.g., sample chest images) associated with the specific object type. As another example, the processing device 120a may obtain one or more features (e.g., a scanning mode, a posture of the object) associated with the type of the scanning device upon which the image is obtained and determine a scanning device type (e.g., a CT device, an MRI device, a PET device) based on the one or more features. Further, the processing device 120a may select an image processing model corresponding to the scanning device type. As used herein, an imaging processing model corresponding to a specific scanning device type may refer to that the image processing model (e.g., an image processing model corresponding to a CT device) is trained based on a plurality of training samples (e.g., sample CT images) associated with the specific scanning device type. More descriptions regarding the image processing model corresponding to an object type and/or a scanning device type may be found elsewhere in the present disclosure (e.g., FIGS. 7 and 8 and the descriptions thereof).

In some embodiments, as described in connection with operation 510, the image to be processed may be a reconstructed image, accordingly, the initial feature of the image may include a reconstruction algorithm based on which the image is obtained. The processing device 120a may select an image processing model based on the reconstruction algorithm. As used herein, an image processing model corresponding to a specific reconstruction algorithm may refer to that the image processing model (e.g., an image processing model corresponding to an iterative reconstruction algorithm) is trained based on a plurality of training samples (e.g., sample reconstructed images) associated with the specific reconstruction algorithm.

In some embodiments, since different reconstruction algorithms may introduce different noise types and/or artifact types. It can be considered that the processing device 120a may select an image processing model based on a noise type or an artifact type. Similarly, an image processing model corresponding to a specific noise type may refer to that the image processing model (e.g., an image processing model corresponding to a Gaussian noise) is trained based on a plurality of training samples (e.g., sample noise images) associated with the specific noise type; and an image processing model corresponding to a specific artifact type may refer to that the image processing model (e.g., an image processing model corresponding to a strip artifact) is trained based on a plurality of training samples (e.g., sample artifact images) associated with the specific artifact type.

In some embodiments, the processing device 120a may obtain the image processing model from a storage device (e.g., the storage device 150, the storage 220, and/or the storage 390) of the medical system 100 or an external resource via a network (e.g., the network 140). For example, the image processing model may be previously trained by a training device (e.g., the processing device 120b) and stored in the storage device of the medical system 100. The processing device 120a may access the storage device and retrieve the image processing model. In some embodiments, the image processing model may be generated by a training device (e.g., the processing device 120b) according to a training process (e.g., process 600, process 700, process 800). More descriptions regarding the image processing model may be found elsewhere in the present disclosure (e.g., FIGS. 6-9 and the descriptions thereof).

In some embodiments, the processing device 120a may directly input the image and the quality feature into the image processing model. In some embodiments, before inputting the image and the quality feature into the image processing model, the processing device 120*a* may preprocess the image by performing an operation on the image such as image resampling, image normalization, etc. Merely by way of example, the processing device 120*a* may determine a resampled image with a preset size by performing an image resampling on the image resample the image. Then the processing device 120*a* may normalize the resampled image such that pixel (or voxel) values of the normalized image may be within a preset range (e.g., [−1, 1]). Further, the processing device 120*a* may input the normalized image and the quality feature into the image processing model.

In 540, the processing device 120*a* (e.g., the optimization module 430) may determine an optimized image of the image based on an output of the image processing model.

In some embodiments, if the image and the quality feature are directly input into the image processing model, the processing device 120*a* may designate the output of the image processing model as the optimized image. In some embodiments, if the image is preprocessed and the preprocessed image and the quality feature are input into the image processing mode, the processing device 120*a* may generate the optimized image by post-processing (e.g., de-normalizing and/or resampling) the output of the image processing model.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations of the process 500 may be omitted and/or one or more additional operations may be added. For example, a storing operation may be added elsewhere in the process 500. In the storing operation, the processing device 120*a* may store information and/or data (e.g., the optimized image) associated with the medical system 100 in a storage device (e.g., the storage device 150) disclosed elsewhere in the present disclosure. As another example, an additional operation for transmitting the optimized image to one or more components (e.g., the terminal device 130) of the medical system 100 for display or further processing may be added after operation 540. In some embodiments, two or more operations in the process 500 may be combined as a single operation. For example, operations 530 and 540 may be combined as a single operation in which the processing device 120*a* may both input the image and the quality feature into the image processing model and generate the optimized image.

Figure 6:
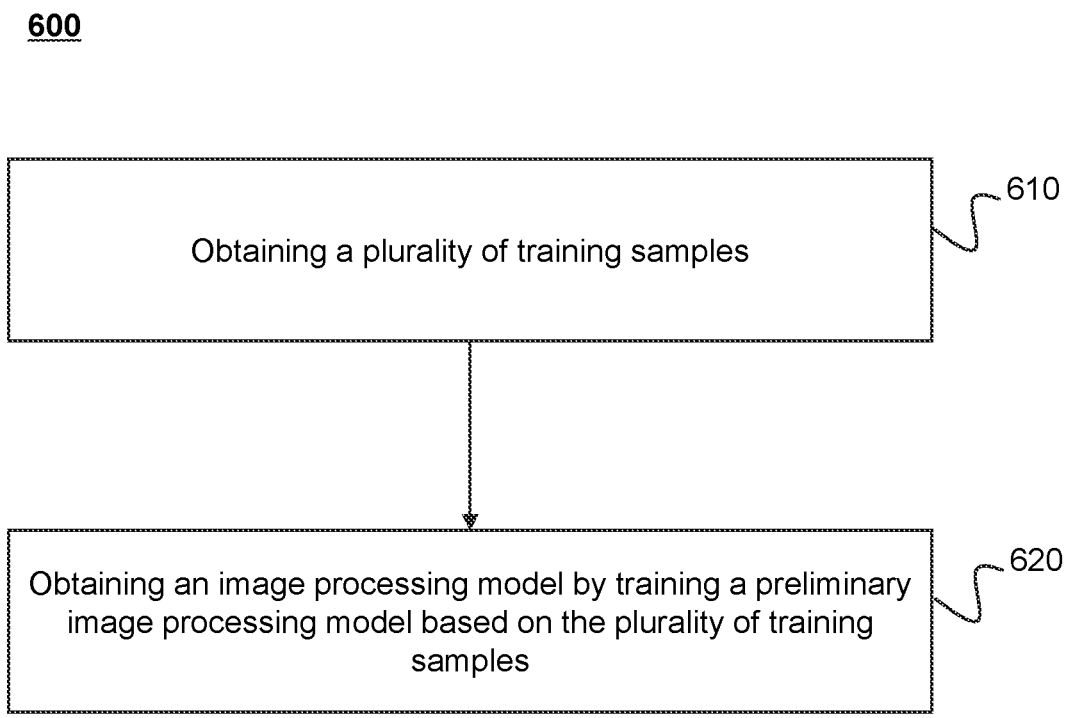
FIG. 6 is a flowchart illustrating an exemplary process for obtaining an image processing model according to some embodiments of the present disclosure.

FIG. 6 is a flowchart illustrating an exemplary process for obtaining an image processing model according to some embodiments of the present disclosure. In some embodiments, the process 600 may be performed by the processing device 120*b* online or offline. For example, process 600 may be implemented as a set of instructions (e.g., an application) stored in a storage device (e.g., the storage device 150, storage 220, and/or storage 390). The processing device 120*b* (e.g., the processor 210, the CPU 340, and/or one or more modules illustrated in FIG. 4B) may execute the set of instructions, and when executing the instructions, the processing device 120*b* may be configured to perform the process 600. The operations of the illustrated process presented below are intended to be illustrative. In some embodiments, the image processing model described in operation 530 in FIG. 5 may be obtained according to the process 600.

In 610, the processing device 120*b* (e.g., the obtaining module 440) may obtain a plurality of training samples.

In some embodiments, each of the plurality of training samples may include a sample image, a sample quality feature of the sample image, etc. As described in connection with operation 520, the sample quality feature may include a sample noise feature, a sample artifact feature, a sample gray distribution, a sample global gray scale, a sample resolution, a sample contrast of the sample image, or the like, or any combination thereof. The sample noise feature may include a sample noise distribution, a sample noise intensity, a sample global noise intensity, a sample noise rate, or the like, or any combination thereof. The sample artifact feature may include a sample artifact distribution, a sample artifact intensity, a sample global artifact intensity, a sample artifact rate, or the like, or any combination thereof.

In some embodiments, the plurality of training samples may correspond to various quality levels (e.g., various noise intensities, various artifact intensities). In some embodiments, the plurality of training samples may be previously generated and stored in a storage device (e.g., the storage device 150, the storage 220, the storage 390, or an external database) disclosed elsewhere in the present disclosure. The processing device 120*b* may retrieve the plurality of training samples directly from the storage device. In some embodiments, at least a portion of the plurality of training samples may be generated by the processing device 120*b*. Merely by way of example, the processing device 120*b* may obtain at least one qualified image. The qualified image used herein may refer to an image with its quality feature satisfying a quality requirement, for example, an image with its SNR greater than an SNR threshold. The SNR of an image may be associated with a radiation does used to obtain the image. The greater the radiation does is, the higher the SNR of the image may be. The processing device 120*b* may generate a plurality of sample images based on the at least one qualified image. For example, the processing device 120*b* may generate the plurality of sample images by preprocessing (e.g., performing a segmentation, a noise addition, an artifact addition) the at least one qualified image. More descriptions regarding the plurality of training samples may be found elsewhere in the present disclosure (e.g., FIGS. 7-9 and the descriptions thereof).

In 620, the processing device 120*b* (e.g., the training module 450) may obtain the image processing model by training a preliminary image processing model based on the plurality of training samples.

In some embodiments, the preliminary image processing model may include a deep learning model such as a DNN model, an MLP model, a CNN model, a GAN model, a DCED network model, etc. In some embodiments, the preliminary image processing model may include at least one preliminary model parameter. The at least one preliminary model parameter may be a default setting of the medical system 100 or may be adjustable under different situations. Take a CNN model as an example, the at least one preliminary model parameter may include a count of convolutional layers, a count of kernels, a kernel size, a stride, a padding of each convolutional layer, or the like, or any combination thereof.

In some embodiments, the processing device 120*b* may train the preliminary image processing model iteratively until a termination condition is satisfied. In response to that the termination condition is satisfied, the image processing model may be finalized. In some embodiments, the termination condition may relate to a value of a loss function. For example, the termination condition may be satisfied if the value of the loss function is minimal or smaller than a predetermined threshold. As another example, the termination condition may be satisfied if the value of the loss function converges. In some embodiments, "convergence" may refer to that the variation of the values of the loss function in two or more consecutive iterations is equal to or smaller than a predetermined threshold. In some embodiments, "convergence" may refer to that a difference between the value of the loss function and a target value is equal to or smaller than a predetermined threshold. In some embodiments, the termination condition may be satisfied when a specified count of iterations have been performed in the training process.

In some embodiments, the loss function may be positively related to a quality weight which may be associated with a quality level of a sample image and may be determined based on the sample quality feature of the sample image. For example, the loss function in a current iteration may be determined according to equation (1) below:

$$L = \sum_1^n w_i * l(f(x_i), y_i); \qquad (1)$$

where L denotes the loss function, n denotes a count of the plurality of training samples, $x_i$ denotes a sample image (can be referred to as an "ith sample image") in an ith training sample, $f(x_i)$ denotes an ith estimated optimized image corresponding to the ith sample image, $y_i$ denotes an ith qualified image (which is used as a ground truth) corresponding to the ith sample image, $l(f(x_i), y_i)$ denotes a loss (e.g., a square loss, an absolute loss) associated with a difference between the ith estimated optimized image and the ith qualified image, and $w_i$ denotes an ith quality weight corresponding to the ith training sample.

In some embodiments, the loss function may be further normalized according to equation (2) below:

$$L = \sum_1^n \frac{w_i * l(f(x_i), y_i)}{m_i^c}, \qquad (2)$$

where $m_i$ denotes an ith sample quality feature of the ith sample image and c denotes a constant which is used to control a nominalization degree of the sample quality feature.

In some embodiments, different training samples may correspond to different quality weights. Take a specific training sample as an example, the quality weight may be determined based on one or more sample quality features of the sample image in the training sample. For example, for each of the one or more sample quality features, the processing device 120b may determine a quality sub-weight corresponding to the sample quality feature. Further, the processing device 120b may determine the quality weight based on one or more quality sub-weights corresponding to the one or more sample quality features. For example, the processing device 120b may determine a comprehensive result (e.g., a weighted sum, a product, an average) of the one or more quality sub-weights as the quality weight.

In some embodiments, the quality weight and/or the quality sub-weight may be negatively or positively related to the sample quality feature(s) according to different optimization targets, so as to balance effects of different samples on the training of the model. For example, for a model used for "noise reduction," the plurality of training samples may include samples with relatively high sample noise intensities and samples with relatively low sample noise intensities. During the training, the loss function may be easy to decrease by optimizing the samples with relatively high sample noise intensities. Therefore, in order balance effects of the samples with relatively high sample noise intensities and the samples with relatively low sample noise intensities on the loss function, quality weights corresponding to the samples with relatively high sample noise intensities may be less than quality weights corresponding to the samples with relatively low sample noise intensities. Merely by way of example, the quality weight may be inversely proportional to the sample noise intensity. From another point of view, the plurality of training samples may include samples with relatively high sample contrasts (e.g., sample CT images including objects with relatively high structure contrasts such as a bone, a lung) and samples with relatively low sample contrasts (e.g., sample CT images including objects with relatively low structure contrasts such as a soft tissue (e.g., a liver)). During the training, the loss function may be easy to decrease by optimizing the samples with relatively high sample contrasts. Therefore, in order balance effects of the samples with relatively high sample contrasts and the samples with relatively low sample contrasts on the loss function, quality weights corresponding to the samples with relatively high sample contrasts may be less than quality weights corresponding to the samples with relatively low sample contrasts. Merely by way of example, the quality weight may be inversely proportional to the sample contrast.

As another example, similarly, for a model used for "artifact reduction," quality weights corresponding to samples with relatively high artifact intensities may be less than quality weights corresponding to samples with relatively low artifact intensities. Merely by way of example, the quality weight may be inversely proportional to the sample artifact intensity.

As a further example, for a model used for "resolution enhancement," the plurality of training samples may include samples with relatively high sample resolutions and samples with relatively low sample resolutions. During the training, the loss function may be easy to decrease by optimizing the samples with relatively low sample resolutions. Therefore, in order balance effects of the samples with relatively high sample resolutions and the samples with relatively low sample resolutions on the loss function, quality weights corresponding to the samples with relatively high sample resolutions may be greater than quality weights corresponding the samples with relatively low sample resolutions. Merely by way of example, the quality weight may be proportional to the sample resolution.

In some embodiments, the quality weight may be expressed as equation (3) below:

$$w_i = A_i^x + B_i^y; \qquad (3)$$

where $w_i$ denotes an ith quality weight corresponding to the ith training sample, $A_i$ denotes a first sample quality feature of the ith training sample, $B_i$, denotes a second sample quality feature of the ith training sample, $A_i^x$ denotes a first quality sub-weight corresponding to the first sample quality feature, $B_i^y$ denotes a second quality sub-weight corresponding to the second sample quality feature, and x and y may be greater than or less than zero. When the value of x (or y) is greater than zero, the quality weight may be positively related to the first sample quality feature (or the second quality feature); when the value of x (or y) is less than zero, the quality weight may be negatively related to the first sample quality feature (or the second quality feature). The values of x and y may be default settings of the medical system 100 or set by an operator of the medical system 100 to balance effects of the first sample quality feature and the second sample quality feature on the training of the model.

In some embodiments, the processing device 120b may determine different image processing models corresponding to different object types and/or different scanning device types. More descriptions can be found elsewhere in the present disclosure (e.g., FIGS. 7-8 and the descriptions thereof). In some embodiments, the processing device 120b may determine different image processing models corresponding to different noise types and/or different artifact types.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations of the process 600 may be omitted and/or one or more additional operations may be added. For example, a storing operation may be added in the process 600. In the storing operation, the processing device 120b may store data (e.g., the image processing model) associated with the medical system 100 in a storage device (e.g., the storage device 150) disclosed elsewhere in the present disclosure. As another example, after the image processing model is generated, the processing device 120b may further test the image processing model using a set of testing samples. Additionally or alternatively, the processing device 120b may update the image processing model periodically or irregularly based on one or more newly-generated training images (e.g., new sample images, new qualified images generated in medical diagnosis).

Figure 7:
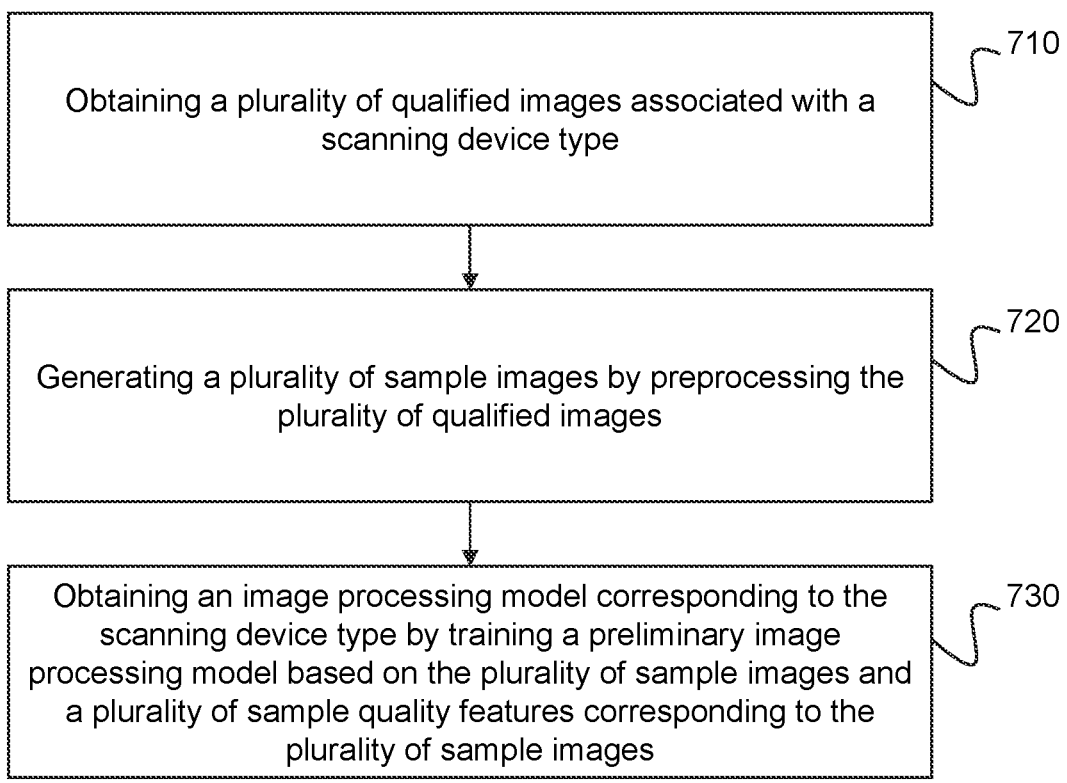
FIG. 7 is a flowchart illustrating an exemplary process for obtaining an image processing model corresponding to a scanning device type according to some embodiments of the present disclosure.

FIG. 7 is a flowchart illustrating an exemplary process for obtaining an image processing model corresponding to a scanning device type according to some embodiments of the present disclosure. In some embodiments, the process 700 may be performed by the processing device 120b online or offline. In some embodiments, process 700 may be implemented as a set of instructions (e.g., an application) stored in a storage device (e.g., the storage device 150, storage 220, and/or storage 390). The processing device 120b (e.g., the processor 210, the CPU 340, and/or one or more modules illustrated in FIG. 4B) may execute the set of instructions, and when executing the instructions, the processing device 120b may be configured to perform process 700. The operations of the illustrated process presented below are intended to be illustrative. In some embodiments, process 500 may be performed based on one or more operations of process 700.

In 710, the processing device 120b (e.g., the obtaining module 440) may obtain a plurality of qualified images associated with a scanning device type.

As described elsewhere in the present disclosure, a qualified image may refer to an image with its quality feature satisfying a quality requirement, accordingly, a qualified image associated with a scanning device type may refer to a qualified image generated by a scanning device of the scanning device type. For example, for a CT device, the plurality of qualified images associated with the scanning device type may include a plurality of qualified CT images. As another example, for a PET device, the plurality of qualified images associated with the scanning device type may include a plurality of qualified PET images.

In some embodiments, the plurality of qualified images may be pre-generated and stored in a storage device (e.g., the storage device 150, the storage 220, the storage 390, or an external database) disclosed elsewhere in the present disclosure. The processing device 120b may retrieve the plurality of qualified images directly from the storage device. In some embodiments, the processing device 120a may generate the plurality of qualified images based on scanning data generated by the scanning device of the scanning device type.

In 720, the processing device 120b (e.g., the obtaining module 440) may generate a plurality of sample images by preprocessing the plurality of qualified images.

In some embodiments, the preprocessing may include segmentation, noise addition, artifact addition, or the like, or any combination thereof. For example, take a specific qualified image as an example, the processing device 120b may segment the qualified image into a plurality of sub-images using an image segmentation algorithm. Exemplary image segmentation algorithms may include a threshold-based segmentation algorithm, an edge-based segmentation algorithm, a region-based segmentation algorithm, a clustering-based algorithm, an image segmentation algorithm based on wavelet transform, an image segmentation algorithm based on mathematical morphology, an image segmentation algorithm based on artificial neural network, or the like, or any combination thereof. As another example, the processing device 120a may add different interference information (e.g., noises and/or artifacts with different levels) into a qualified image or a sub-image to generate a plurality of sample images corresponding to the qualified image or the sub-image. In some embodiments, the processing device 120b may add noises of different types (e.g., a Gaussian noise, an impulse noise, a Rayleigh noise, an exponential distribution noise, a uniform distribution noise, a random noise) with different levels into the qualified image or the sub-image. Similarly, the processing device 120b may add artifacts of different types (e.g., a strip artifact, a ring artifact, a shadow artifact, a ribbon artifact, a Windmill artifact, a pinwheel artifact, a streaking artifact, a motion artifact) with different levels into different regions of the qualified image or the sub-image.

Figure 9:
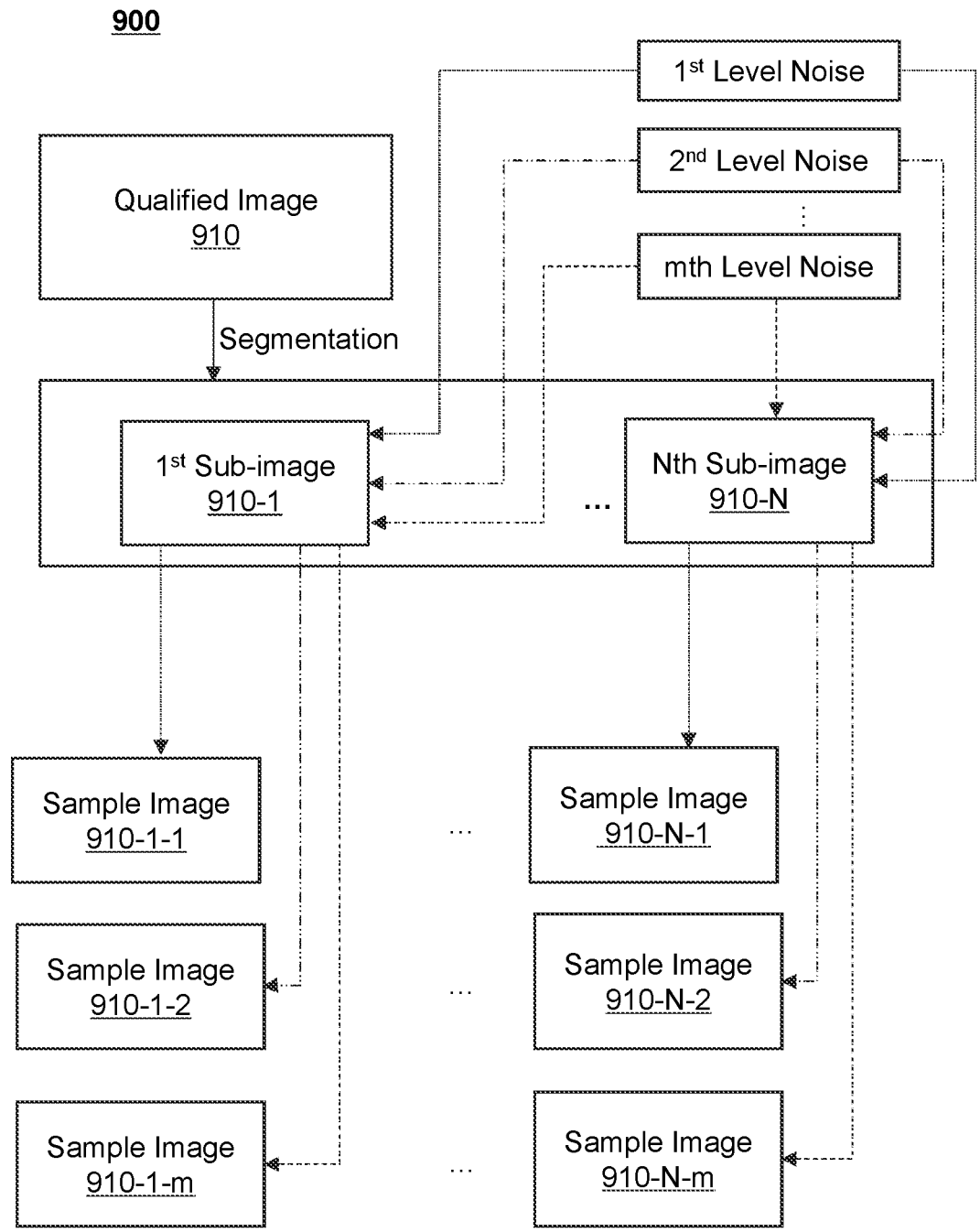
FIG. 9 is a schematic diagram illustrating an exemplary process for determining a plurality of sample images based on a qualified image according to some embodiments of the present disclosure.

As shown in FIG. 9, the processing device 120b may segment a qualified image 910 to a plurality of sub-images including a sub-image 910-1, a sub-image 910-2 (not shown), . . . , and a sub-image 910-N. The processing device 120b may add noises with different levels (e.g., a 1st level noise, a 2nd level noise, . . . , an mth level noise) to each of the plurality of sub-images, respectively. For the sub-image 910-1, the processing device 120b may generate a plurality of first sample images including a sample image 910-1-1, a sample image 910-1-2, . . . , and a sample image 910-1-m. For the sub-image 910-N, the processing device 120b may generate a plurality of Nth sample images including a sample image 910-N-1, a sample image 910-N-2, . . . , and a sample image 910-N-m.

In 730, the processing device 120b (e.g., the training module 450) may obtain the image processing model corresponding to the scanning device type by training a preliminary image processing model based on the plurality of sample images and a plurality of sample quality features corresponding to the plurality of sample images.

In some embodiments, the processing device 120b may obtain a preliminary image processing model as described elsewhere in the present disclosure. The processing device 120b may obtain the plurality of sample quality features corresponding to the plurality of sample images. The processing device 120b may generate the image processing model corresponding to the scanning device type by training the preliminary image processing model based on the plurality of sample images and the plurality of sample quality features. The training of the preliminary image processing image model may be the same as or similar to that described in operation 620 in FIG. 6, and is not repeated here.

Figure 8:
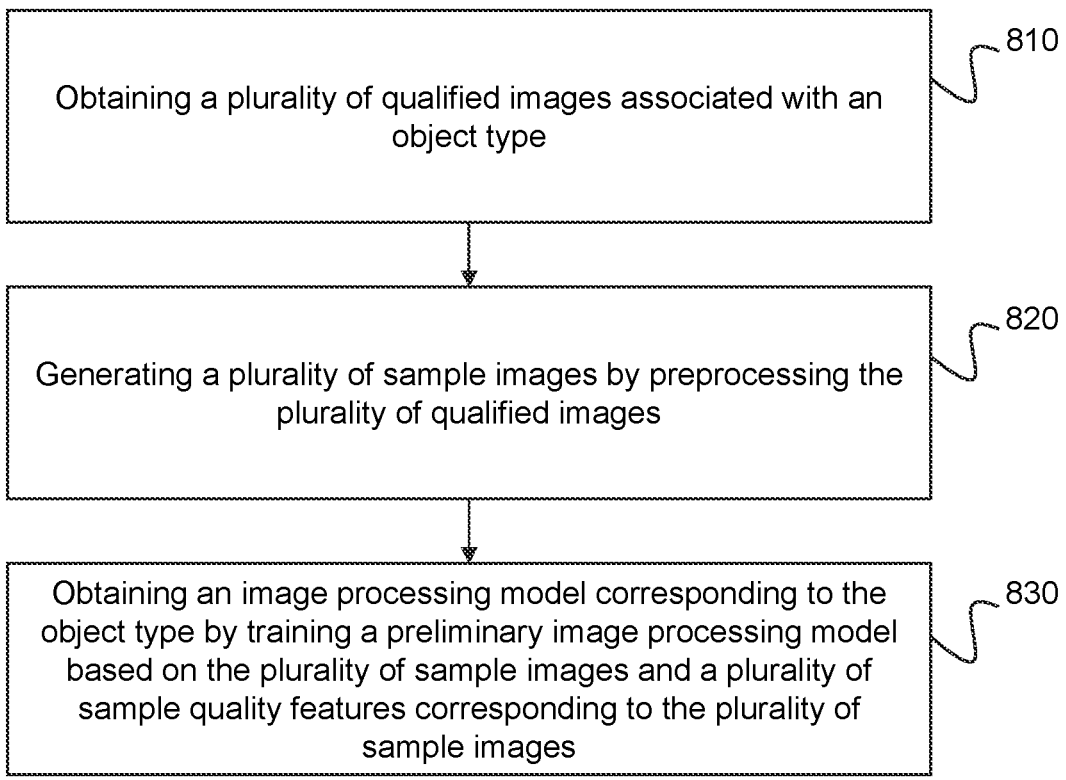
FIG. 8 is a flowchart illustrating an exemplary process for obtaining an image processing model corresponding to an object type according to some embodiments of the present disclosure.

FIG. 8 is a flowchart illustrating an exemplary process for obtaining an image processing model corresponding to an object type according to some embodiments of the present disclosure. In some embodiments, the process 800 may be performed by the processing device 120b online or offline. In some embodiments, process 800 may be implemented as a set of instructions (e.g., an application) stored in a storage device (e.g., the storage device 150, storage 220, and/or storage 390). The processing device 120b (e.g., the processor 210, the CPU 340, and/or one or more modules illustrated in FIG. 4B) may execute the set of instructions, and when executing the instructions, the processing device 120b may be configured to perform process 800. The operations of the illustrated process presented below are intended to be illustrative. In some embodiments, process 500 may be performed based on one or more operations of process 800.

In 810, the processing device 120b (e.g., the obtaining module 440) may obtain a plurality of qualified images associated with the object type.

As described elsewhere in the present disclosure, a qualified image may refer to an image with its quality feature satisfying a quality requirement, accordingly, a qualified image associated with an object type may refer to a qualified image including an object of the object type. For example, for an object type "chest," the plurality of qualified images associated with the object type may include a plurality of qualified chest images. As another example, for an object type "head," the plurality of qualified image associated with the object type may include a plurality of qualified head images.

In some embodiments, the plurality of qualified images may be pre-generated and stored in a storage device (e.g., the storage device 150, the storage 220, the storage 390, or an external database) disclosed elsewhere in the present disclosure. The processing device 120b may retrieve the plurality of qualified images directly from the storage device. In some embodiments, the processing device 120a may generate the plurality of qualified images based on scanning data associated with the object type.

In 820, the processing device 120b (e.g., the obtaining module 440) may generate a plurality of sample images by preprocessing the plurality of qualified images.

In some embodiments, the preprocessing may include segmentation, noise addition, artifact addition, or the like, or any combination thereof. The generation of the plurality of sample image may be similar to or the same as that described in operation 720 in FIG. 7, and is not repeated herein.

In 830, the processing device 120b (e.g., the training module 450) may obtain the image processing model corresponding to the object type by training a preliminary image processing model based on the plurality of sample images and a plurality of sample quality features corresponding to the plurality of sample images.

In some embodiments, the processing device 120b may obtain a preliminary image processing model as described elsewhere in the present disclosure. The processing device 120b may obtain the plurality of sample quality features corresponding to the plurality of sample images. The processing device 120b may generate the image processing model corresponding to the object type by training the preliminary image processing model based on the plurality of sample images and the plurality of sample quality features. The training of the preliminary image processing image model may be the same as or similar to that described in operation 620 in FIG. 6, and is not repeated here.

It should be noted that the above descriptions regarding the processes 700 and 800 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. The operations of the illustrated process presented above are intended to be illustrative. In some embodiments, the process 700 and/or process 800 may be accomplished with one or more additional operations not described and/or without one or more of the operations discussed. Additionally, the order of the operations of the process 700 and/or the process 800 is not intended to be limiting.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:

1. A method for medical image optimization, comprising:
   obtaining an initial image to be processed acquired by a medical scanning device;
   determining a quality feature of the initial image;
   inputting the initial image and the quality feature into an image processing model, wherein a loss function of the image processing model for training is positively related to a quality weight, and the quality weight being determined based on a sample quality feature of each of a plurality of training samples for the training of the image processing model and wherein the quality weight of the training sample is determined based on a first quality sub-weight corresponding to a first sample quality feature of the training sample and a second quality sub-weight corresponding to a second sample quality feature of the training sample; and
   determining an optimized image of the initial image based on an output of the image processing model.

2. The method of claim 1, wherein the method further includes:
   selecting the image processing model based on an initial feature of the initial image to be processed, wherein the initial feature includes at least one of a feature associated with an object included in the initial image, a feature associated with a type of a scanning device upon which the initial image is obtained, or a reconstruction algorithm based on which the initial image is obtained.

3. The method of claim 1, wherein the quality feature further includes at least one of a noise feature, an artifact feature, a gray distribution, a global gray scale, a resolution, or a contrast of the image.

4. The method of claim 3, wherein
   the noise feature includes at least one of a noise distribution, a noise intensity, or a noise rate; or the artifact feature includes at least one of an artifact distribution, an artifact intensity, or an artifact rate.

5. The method of claim 1, wherein the image processing model is obtained by a training process including:
   obtaining the plurality of training samples, each of the plurality of training samples including a sample image and the sample quality feature of the sample image; and
   obtaining the image processing model by training a preliminary image processing model based on the plurality of training samples.

6. The method of claim 5, wherein the sample quality feature includes at least one of a sample noise feature, a sample artifact feature, a sample gray distribution, a sample global gray scale, a sample resolution, or a sample contrast of the sample image.

7. The method of claim 6, wherein
   the sample noise feature includes at least one of a sample noise distribution, a sample noise intensity, or a sample noise rate; or
   the sample artifact feature includes at least one of a sample artifact distribution, a sample I artifact intensity, or a sample artifact rate.

8. The method of claim 7, wherein
   the quality weight is positively related to the sample resolution;
   the quality weight is negatively related to the sample noise intensity;
   the quality weight is negatively related to the sample artifact intensity; or
   the quality weight is negatively related to the sample contrast.

9. The method of claim 1, the image processing model is obtained by a training process including:
   obtaining a plurality of qualified images associated with a scanning device type;
   generating a plurality of sample images by preprocessing the plurality of qualified images, wherein the preprocessing includes at least one of a segmentation, a noise addition, or an artifact addition; and
   obtaining the image processing model by training a preliminary image processing model based on the plurality of sample images and a plurality of sample quality features corresponding to the plurality of sample images.

10. The method of claim 1, wherein the image processing model is obtained by a training process including:
   obtaining a plurality of qualified images associated with an object type;
   generating a plurality of sample images by preprocessing the plurality of qualified images, wherein the preprocessing includes at least one of a segmentation, a noise addition, or an artifact addition; and
   obtaining the image processing model by training a preliminary image processing model based on the plurality of sample images and a plurality of sample quality features corresponding to the plurality of sample images.

11. The method of claim 1, wherein the image processing model is a deep learning model, the deep learning model including a deep neural network (DNN) model, a multi-layer perceptron (MLP) model, a conventional neural network (CNN) model, a generative adversarial network (GAN) model, or a deep convolutional encoder-decoder (DCED) network model.

12. The method of claim 1, wherein the loss function in a current iteration is determined based on a weighted loss by weighting, based on the quality weight corresponding to the training sample, a loss associated with a difference between an estimated optimized image of the training sample and a qualified image.

13. The method of claim 1, wherein the loss function in a current iteration is determined based on the sample quality feature of the training sample and a weighted loss by weighting, based on the quality weight corresponding to the training sample, a loss associated with a difference between an estimated optimized image of the training sample and a qualified image.

14. A system for medical image optimization, comprising:
   at least one storage device including a set of instructions; and
   at least one processor configured to communicate with the at least one storage device, wherein when executing the set of instructions, the at least one processor is configured to direct the system to perform operations including:
      obtaining an initial image to be processed acquired by a medical scanning device;
      determining a quality feature of the initial image;
      inputting the initial image and the quality feature into an image processing model, wherein a loss function of the image processing model for training is positively related to a quality weight, and the quality weight being determined based on a sample quality feature of each of a plurality of training samples for the training of the image processing model and wherein the quality weight of the training sample is determined based on a first quality sub-weight corresponding to a first sample quality feature of the training sample and a second quality sub-weight corresponding to a second sample quality feature of the training sample; and
      determining an optimized image of the initial image based on an output of the image processing model.

15. The system of claim 14, wherein the operations further include:
   selecting the image processing model based on an initial feature of the initial image to be processed, wherein the initial feature includes at least one of a feature associated with an object included in the initial image, a feature associated with a type of a scanning device upon which the initial image is obtained, or a reconstruction algorithm based on which the initial image is obtained.

16. The system of claim 14, wherein the quality feature further includes at least one of a noise feature, an artifact feature, a gray distribution, a global gray scale, a resolution, or a contrast of the image.

17. The system of claim 16, wherein
   the noise feature includes at least one of a noise distribution, a noise intensity, or a noise rate; or
   the artifact feature includes at least one of an artifact distribution, an artifact intensity, or an artifact rate.

18. The system of claim 14, wherein the image processing model is obtained by a training process including:
   obtaining a plurality of training samples, each of the plurality of training samples including a sample image and a sample quality feature of the sample image; and
   obtaining the image processing model by training a preliminary image processing model based on the plurality of training samples, wherein a loss function of the image processing model is positively related to a quality weight, the quality weight being determined based on the sample quality feature.

19. A method for medical image optimization, comprising:
- obtaining raw image data to be processed acquired by a medical scanning device;
- determining a quality feature of the raw image data;
- inputting the raw image data and the quality feature into an image processing model, wherein a loss function of the image processing model for training is positively related to a quality weight, and the quality weight being determined based on a sample quality feature of each of a plurality of training samples for the training of the image processing model and wherein the quality weight of the training sample is determined based on a first quality sub-weight corresponding to a first sample quality feature of the training sample and a second quality sub-weight corresponding to a second sample quality feature of the training sample; and
- determining optimized image data of the raw image data based on an output of the image processing model.

* * * * *